(12) United States Patent
Kalfas (10) Patent No.: US 6,267,596 B1
(45) Date of Patent: Jul. 31, 2001

(54) DENTAL APPLIANCE

(76) Inventor: Lawrence Leroy Kalfas, 1860 West Dr., Hinckley, OH (US) 44233

( * ) Notice: Subject to any disclaimer, the term of this patent is extended or adjusted under 35 U.S.C. 154(b) by 0 days.

(21) Appl. No.: 09/224,395

(22) Filed: Dec. 31, 1998

(51) Int. Cl.$^7$ ............................................... A61C 13/225
(52) U.S. Cl. .......................................................... 433/178
(58) Field of Search .................................... 433/167, 177, 433/178, 190, 191, 193, 194, 195

(56) References Cited

U.S. PATENT DOCUMENTS

| | | | | |
|---|---|---|---|---|
| 2,789,350 | * | 4/1957 | Fischer | 433/178 |
| 3,271,858 | | 9/1966 | Simmons . | |
| 4,014,094 | * | 3/1977 | Schumann | 433/178 |
| 4,024,636 | * | 5/1977 | Colpetts et al. . | |
| 4,184,253 | * | 1/1980 | Tureaud | 433/171 |
| 4,764,115 | * | 8/1988 | Willits et al. | 433/177 |
| 4,917,605 | * | 4/1990 | Hallmark | 433/178 |
| 5,151,279 | * | 9/1992 | Kimura . | |
| 5,324,186 | * | 6/1994 | Bakanowski . | |
| 5,364,269 | * | 11/1994 | Willits et al. | 433/178 |

OTHER PUBLICATIONS

Brochure, SwingLock Clinical Manual, no date.
6 pages, Material Safety Data Sheet, Valplast Resin, no date.
1 page letter, MicroSelect "Are you seriuosly interested in cosmetic dentistry . . . ?", date unkown.
Selected pages and figures, Valprast Processing Technique, 1995.
Advertisement, Roe Dental Laboratory, "A Winning Combination", date unkown.
Brochure, Dental D, "Acetal Resin Injection System", date unknown.
8 page letter, Lab One, "Virginia Partial", Dec. 1993.
4 page Newsletter, Roe Report, "Prosthetic Newsletter", Spring 1998.

* cited by examiner

Primary Examiner—Ralph A. Lewis
(74) Attorney, Agent, or Firm—Watts, Hoffman, Fisher & Heinke Co., L.P.A.

(57) ABSTRACT

A dental appliance includes a lingual section adapted to engage at least one abutment tooth. A first tissue replacement portion extends from one end portion of the lingual section. A second tissue replacement portion extends from another end portion of the lingual section. A buccal or labial gate is adapted to engage the at least one abutment tooth. A hinge is partially formed by an end portion of the gate. A latch may be disposed at another end portion of the gate. The end portion of the gate is comprised of a tissue replacement material. The dental appliance is made by forming the hinge portion and/or the latch portion of the gate as well as corresponding hinge and gate recesses in the tissue replacement portions by application of curable tissue replacement material into exposed regions within investment material or by application of secondary curable material to formed components of cured tissue replacement material to selectively bond to certain portions of the tissue replacement portions.

28 Claims, 4 Drawing Sheets

DENTAL APPLIANCE

FIELD OF THE INVENTION

The present invention is directed to removable dental appliances and, in particular, to dental appliances applicable to prosthetic, restorative periodontal and orthodontic dentistry.

BACKGROUND OF THE INVENTION

The loss of natural teeth may warrant the use of a partial denture or dental appliance. Some of the factors that influence the decision as to whether a partial denture is required include shrinkage of the gums, reduction or removal of the alveolar process or foundation that partially supports the dental appliance, and loss of molars which reduces the number of abutments available for anchoring and supporting the appliance. Another difficulty is that the few remaining teeth may be mobile.

One form of partial denture is known as a clasp type partial. The partial includes hook like portions that are formed of metal or plastic and extend around individual abutment teeth to support the dental appliance in the mouth. When one or more of the abutment teeth is lost, the dentist may recommend an alternative dental appliance such as that disclosed in U.S. Pat. No. 3,271,858. The dental appliance of the 3,271,858 patent addresses the difficulties involved with developing and using partial dentures with a design that includes a metal lingual section adapted to engage abutment teeth, a first metal frame section extending from one end of the lingual section for supporting replacement teeth and a second metal frame section extending from the other end of the lingual section for supporting replacement teeth. A metal labial bar extends between the first and second frame sections. Plastic replacement tissue material extends around the replacement teeth that are carried by the first and second frame sections. A metal hinge member is disposed at one side of the labial bar and a metal latch member is disposed at the other side of the labial bar. The labial bar is connected to the hinge so as to be swingably movable relative to the abutment teeth. The labial bar includes a hook type catch that engages the latch member to enable the abutment teeth to be firmly clasped between the lingual section and the labial bar.

A disadvantage of the dental appliance of the 3,271,858 patent is that the labial bar, the hinge member and the latch member are formed of metal. Therefore, clasp type partials cannot easily be restored so as to utilize this design. In addition, although a plastic replacement tissue portion may be carried by the metal labial bar, the labial bar is bulky in the patient's mouth, may cause discomfort and is unsightly.

SUMMARY OF THE INVENTION

In general, the dental appliance of the present invention comprises a lingual section adapted to engage at least one abutment tooth, a first tissue replacement portion extending from one end portion of the lingual section, a second tissue replacement portion extending from another end portion of the lingual section, a gate adapted to engage the at least one abutment tooth at a buccal or labial position and a hinge partially formed by an end portion of the gate, wherein the end portion of the gate is comprised of cured tissue replacement (e.g., plastic) material.

More specifically, the dental appliance may also include a latch disposed at another end portion of the gate. The entire gate including a hinge portion and a latch portion is preferably comprised of nonmetallic, cured material (e.g., plastic) and free of metal reinforcement. The hinge may be comprised of a mechanical interlocking of the gate end portion and the first tissue replacement portion, and pivotally connects the first tissue replacement portion and gate together. Alternatively, the hinge may be a living hinge formed by continuous material between the first tissue replacement portion and the gate. The second tissue replacement portion comprises a recess for receiving a latch portion of the gate. The first and second tissue replacement portions are preferably comprised of plastic such as acrylic, or a polyamide, for example. The gate is comprised of a suitable plastic material such as one of the above plastic materials, preferably a material other than acrylic. In the case of a restoration of a dental appliance, portions of the hinge and the recess may be comprised of secondary acrylic material bonded to acrylic material that comprises the first and second tissue replacement portions. Dental appliances may also be restored using the lost wax process.

The appliance may comprise first and second metal frame sections disposed in the first and second tissue replacement portions, respectively, the first and second frame sections being adapted to support replacement teeth. In one aspect, the lingual section is comprised of metal and is integrally formed with the first and second frame sections. In another aspect, the first and second plastic tissue replacement portions are configured and arranged to support replacement teeth without a metal framework. In the case of restoring clasp-type partial dentures, the first and second tissue replacement portions are comprised of acrylic tissue replacement portions from a clasp-type partial denture.

A preferred embodiment is directed to a dental appliance comprising: a lingual section adapted to engage at least one abutment tooth; a first plastic tissue replacement portion extending from one end portion of the lingual section; a second plastic tissue replacement portion extending from another end portion of the lingual section; a gate adapted to engage the at least one abutment tooth at a buccal or labial position; a hinge comprised of a mechanical interlocking between an end portion of the gate and a portion of the first tissue replacement portion that enables the gate to be swingably movable relative to the abutment teeth, the end portion of the gate being comprised of a curable tissue replacement material; and a latch disposed at another end portion of the gate.

A method of making a dental appliance according to the invention, especially a new appliance, comprises the steps of positioning a replacement tooth-supporting member in investment mold material contained by a vessel. The member includes tissue replacement portions comprised of wax. A hinge form is positioned in the investment mold material. A latch form is positioned in the investment mold material. Wax portions are removed to expose regions that are intended to receive replacement tissue material. Replacement tissue material is applied to the exposed regions. The material is hardened to form a first tissue replacement portion extending from one end portion of a lingual section of the member adapted to engage at least one abutment tooth. A hinge is formed in the first tissue replacement portion. A latch is formed in the second tissue replacement portion.

In the case in which the buccal or labial tissue replacement portion is not present when the plastic tissue replacement portions are injected, the method comprises positioning a wax tissue replacement portion in investment material in the vessel in a buccal or labial opening between the first tissue replacement portion and the second tissue replacement portion, the wax tissue replacement portion including the hinge form and the latch form. The wax material of the wax tissue replacement portion is removed thereby exposing a region intended to receive tissue replacement material. Curable tissue replacement material is applied to the exposed region left by removal of the wax tissue replacement portion. The material is hardened to form a tissue replacement gate including a hinge portion that forms at least a portion of the hinge and a latch portion that forms at least a portion of the latch. The gate is movable such that the at least one abutment tooth can be enclosed by the lingual section and the gate.

Another aspect of the method uses the hinge recess-forming member and the latch recess-forming member as part of a nonmetallic cured buccal or labial tissue replacement gate. In this case, the tissue replacement portions are formed of wax and either alone or using a framework, support the replacement teeth. The wax is removed, exposing regions intended to receive replacement tissue. When the curable material is injected into these regions, the replacement gate prevents the material from filling the region the gate occupies. Therefore, the hinge recess forming member is part of the gate and forms the hinge recess when the material is injected and the latch recess forming member is part of the gate and forms the latch recess when the material is injected.

Another inventive method of making a dental appliance comprising the steps of positioning a buccal or labial tissue replacement gate portion in an opening between a first plastic tissue replacement portion extending from one end portion of a lingual section and a second plastic tissue replacement portion extending from another end portion of the lingual section. The lingual section is adapted to engage at least one abutment tooth. The gate portion has a first hinge portion and the first tissue replacement portion has a second hinge portion. Secondary material (e.g., acrylic) is applied to the first tissue replacement portion and into contact with the hinge form. The material is hardened such that the gate portion can form a gate that is swingably movable via the hinge relative to the at least one abutment tooth. In addition, the method may include applying secondary material (e.g., acrylic) to a recess formed in the second tissue replacement portion and hardening the material to form a latch recess such that the buccal or labial tissue replacement portion can form a gate having a latch portion that can be fastened in the recess. This method is particularly useful in restoring existing dental appliances such as a clasp-type partial denture in which case the clasps are removed from the appliance prior to applying the tissue replacement material. This restoring process preferably includes forming a hinge opening in the first acrylic tissue replacement portion and forming a latch opening in the second acrylic tissue replacement portion, the secondary material being comprised of acrylic which bonds to the acrylic of the first and second tissue replacement portions. The gate, however, is free of acrylic, so the secondary material does not bond to it. Therefore, the hinge recess and the gate recess may be configured around the gate hinge portion and the gate latch portion without bonding to them.

Another feature of the invention is a hinge form adapted to form a hinge on a dental appliance, the hinge form being comprised of wax and having a shape that upon removal of the wax, can form a void that approximates the shape of a hinge component formed of a nonmetallic cured material. Another aspect is a hinge form adapted to form a hinge on a dental appliance, the hinge form being comprised of a nonmetallic, cured material that is incapable of chemically bonding to a denture base material, the hinge form being adapted to form a mechanical hinge between a nonmetallic cured tissue replacement portion of the appliance and a nonmetallic cured gate of the appliance.

Yet another feature of the invention is a latch form adapted to form a latch on a dental appliance, the latch form being comprised of wax and having a shape that upon removal of the wax, can form a void that approximates the shape of a latch component formed of a nonmetallic cured material. Another aspect is a latch form adapted to form a latch on a dental appliance, the latch form being comprised of a nonmetallic, cured material that is incapable of chemically bonding to a denture base material, the latch form being adapted to form a mechanical latch between a non-metallic cured tissue replacement portion of the appliance and a nonmetallic cured gate of the appliance.

Another feature of the invention is a gate for a dental appliance, the gate being shaped to form a buccal or labial tissue replacement portion, the gate being comprised of nonmetallic cured material, the gate comprising at least one of a portion adapted to form at least part of a hinge of the appliance and a portion adapted to form at least part of a latch of the appliance. Another aspect is a gate form for a dental appliance, the gate form being shaped to form a buccal or labial tissue replacement portion, the gate form being comprised of wax and having a shape that upon removal of the wax, can form a void that approximates the shape of at least one of a latch component of the appliance formed of a nonmetallic cured material and a hinge component of the appliance formed of nonmetallic cured material.

The present invention offers numerous advantages compared to previous dental appliances. Clasp-type partial denture appliances are unsightly especially when metal clasps are used. In addition, when few abutment teeth are present, the clasp-type partial denture may not have sufficient support at certain portions remote from the abutments. This may cause shifting when the patient bites down at these unsupported locations. This can lead to discomfort and even to movement of the abutment teeth. The dental appliance of the 3,271,858 patent also suffers from drawbacks. The metal gate is unsightly, may cause the user discomfort due to its bulky size and is not readily adapted for restoring clasp-type partials.

The present invention is advantageous in that it enables easy and reliable fabrication of a dental appliance having a gate with a hinge and/or latch portion that is formed of curable tissue replacement material such as plastic. The use of curable material enables versatility in designing the hinge and latch to correspond to features of the gate. That is, the tissue replacement portions may be formed of plastic with the hinge or latch recesses formed in them by the lost wax process or by physical removal of plastic material. In addition, the plastic of the tissue replacement portions and the gate may be formed with components embedded therein. For example, the hinge form may be embedded in the tissue replacement portion and/or carried by the gate hinge portion during plastic forming. Alternatively, the hinge form may be located in the hinge opening and then secondary plastic material (e.g., acrylic) may be applied to bond to the tissue replacement portion and secure the hinge form in place. These features enable existing dental appliances such as clasp-type partials to utilize the design of the present invention. Such a restoration is not easily accomplished should one attempt to fasten a metal gate as in the 3,271,858 patent to a clasp-type denture. In addition, the inventive use of tissue replacement material for the buccal or labial gate avoids the need for metal reinforcement, thereby reducing the thickness of the gate, increasing its comfort and enhancing its appearance.

Other embodiments of the invention are contemplated to provide particular features and structural variants of the basic elements. The specific embodiments referred to as well as possible variations and the various features and advantages of the invention will become better understood from the accompanying drawings together in connection with the detailed description that follows.

DETAILED DESCRIPTION OF PREFERRED EMBODIMENTS

Referring now to FIGS. 1–3 and 10 of the drawings, the dental appliance of the invention is generally shown at 10 in position on a dental mold. The dental appliance comprises a lingual section 12 adapted to engage at least one natural abutment tooth 14. A first tissue replacement portion 16 extends from one end portion of the lingual section. A second tissue replacement portion 18 extends from the other end portion of the lingual section. A gate 20 is adapted to engage the abutment teeth at a buccal or labial position. A hinge 22 is comprised of a hinge portion 24 at one end portion of the gate, portion(s) 26 of the first tissue replacement portion and a hinge component (e.g., pin 28) that connects the hinge portion of the gate and the first tissue replacement portion to enable the gate to be swingably movable relative to the abutment teeth. The hinge portion of the gate and the first and second tissue replacement portions are comprised of nonmetallic cured tissue replacement material. A latch 30 is disposed at the other end portion of the gate and is comprised of a latch portion 32 extending from the gate and a latch recess 34 formed in the second tissue replacement portion. The dental appliance may also include a framework or major connector 36 (FIG. 8) made of metal, for example, for supporting replacement teeth, the major connector comprising the lingual section 12, a first frame section 38 extending from one end portion of the lingual section and a second frame section 40 extending from the other end portion of the lingual section. Alternatively, the major connector may be formed of cured nonmetallic material (e.g., acrylic) that holds the replacement teeth in place and also comprises the tissue replacement portions without a framework. The lingual section engages the abutment teeth 14 as shown in FIG. 8.

Figure 8:
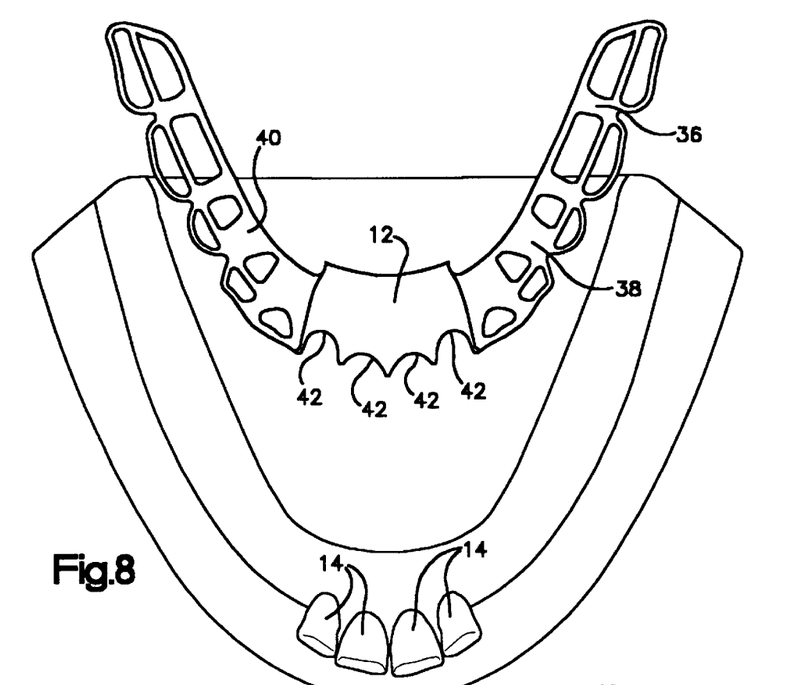
FIG. 8 is a top plan view of a framework of a dental appliance.

The particular natural abutment teeth 14 shown in FIG. 8 that are engaged by the lingual section are merely illustrative. It will be apparent to those skilled in the art that the lingual section can engage the abutment teeth despite variations in their number and location. That is, the gate may be located at a buccal position such that the lingual section and the gate enclose abutment teeth on the side of the mouth or back teeth such as molars. The lingual section may carry one or more replacement teeth at one of the locations 42. The manner of fastening replacement teeth to the frame sections and to the lingual section, and of fabricating the metal framework, are achieved through known processes and materials such as are described in the 3,271,858 patent, which is incorporated herein by reference in its entirety. It will also be apparent to one skilled in the art in view of this disclosure that while the inventive dental appliance is described and illustrated for use in the lower jaw or mandible of a patient, it may also be used on the upper jaw or maxilla of a patient to achieve all of the advantages described herein. Moreover, the locations of the hinge and latch may be reversed; the hinge and latch may be formed on the second tissue replacement portion and on the first tissue replacement portion, respectively.

Figures 1, 2, 3:
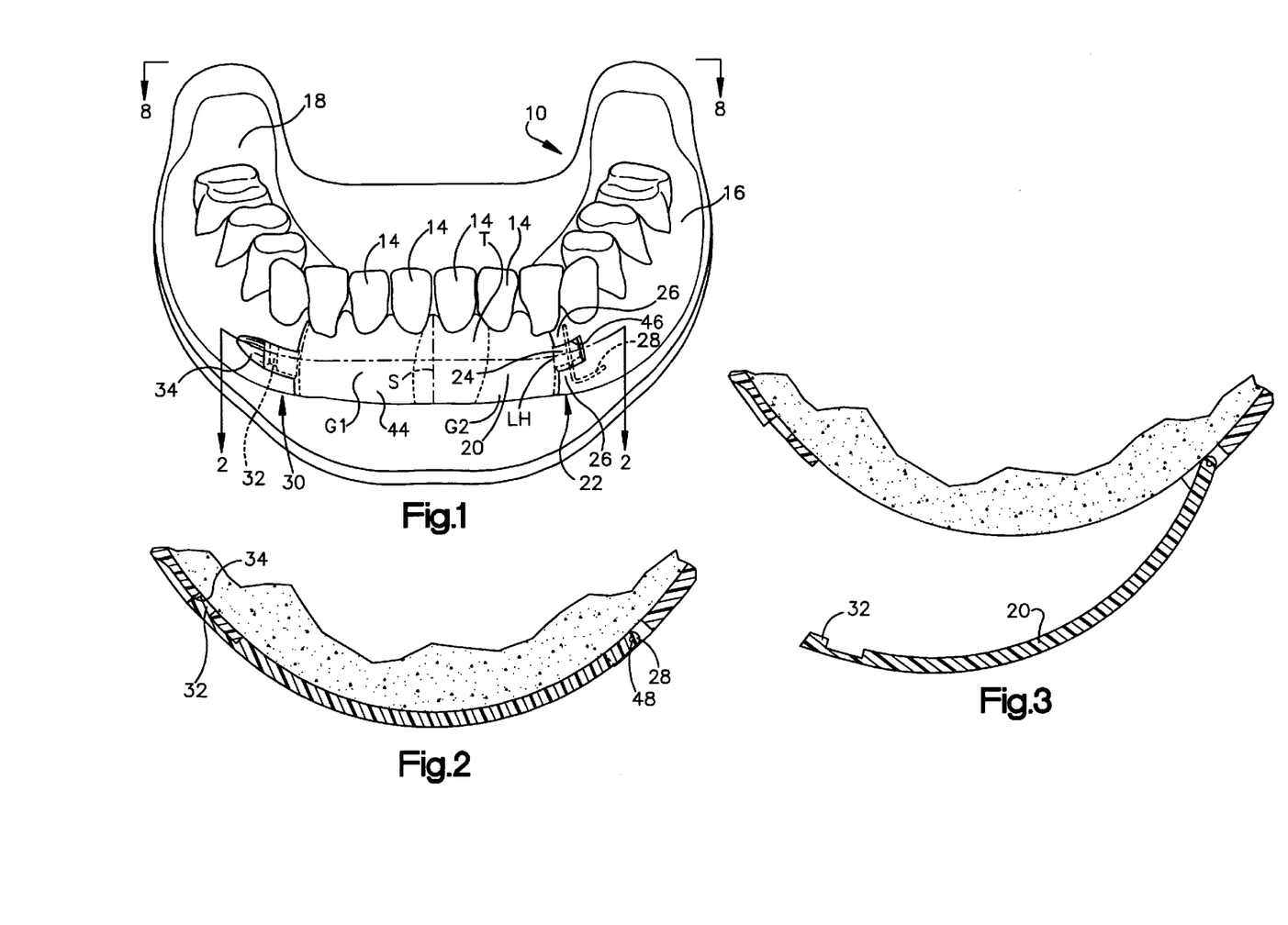
FIG. 1 is a cross-sectional view of a dental appliance constructed in accordance with the present invention.
FIG. 2 is a cross-sectional view as seen along the plane designated by arrows 2—2 in FIG. 1, showing a gate of the appliance in the closed or latched position.
FIG. 3 is a view of the appliance with the gate in the open or unlatched position.

As shown in FIG. 1, in addition to its mechanical locking function the gate functions as a buccal or labial tissue replacement portion 44 comprised of plastic, acrylic or resin material. The first tissue replacement portion includes a recess 46, the recess forming the hinge portions 26 of the tissue replacement material. The hinge pin is embedded in the material of the first tissue replacement portion and extends generally vertically across the recess 46. The hinge pin is preferably formed of metal. At an end portion of the gate the protruding hinge portion 24 extends into the hinge recess. The hinge portion of the gate includes a generally vertically extending hole 48 that receives the hinge pin, thereby enabling the gate to be swingably movable relative to the abutment teeth. It will be understood that the invention is not limited to the particular type of hinge shown, but rather any hinge may be used so long as it is partially or fully formed by a plastic, acrylic or resin portion of the gate. Similarly, the invention is not limited to the type of latch shown and other latches may be suitable for use in the present invention.

In particular, the mechanical hinge of the present invention may be formed of a first hinge portion of the gate and a second hinge portion formed by or embedded within the first tissue replacement portion. For example, the gate or first tissue replacement portion may include an elongated opening(s) and from the other may extend one or more protrusions, pins or pintles that engage the opening. The gate or the tissue replacement portion may have the protrusions integrally formed therewith comprised of the nonmetallic curable materials described. That is, the hinge need not include a separate pin but may be formed solely of the material of the gate and/or tissue replacement portion. Numerous variations of hinge designs which form at least a portion of the hinge from the nonmetallic curable (e.g., plastic) material of the gate, would be apparent to one skilled in the art in view of this disclosure.

One particular variation is a gate formed of two sections G1 and G2 as shown in FIG. 1 separated, for example, as represented by the dotted line S. Such a design would include a hinge at the second tissue replacement portion 18 rather than the latch shown. Such a gate may include a latch formed by the two sections, or in the case when a tissue replacement portion T is present, may form the latch using the nonmetallic, curable (e.g., plastic) of this portion T to form the latch. Alternatively, such a design may include a hinge or hinges near the line S or in the portion T instead of the latch, and latches in place of the two hinges at the ends of each of the sections G1 and G2.

Figure 4:
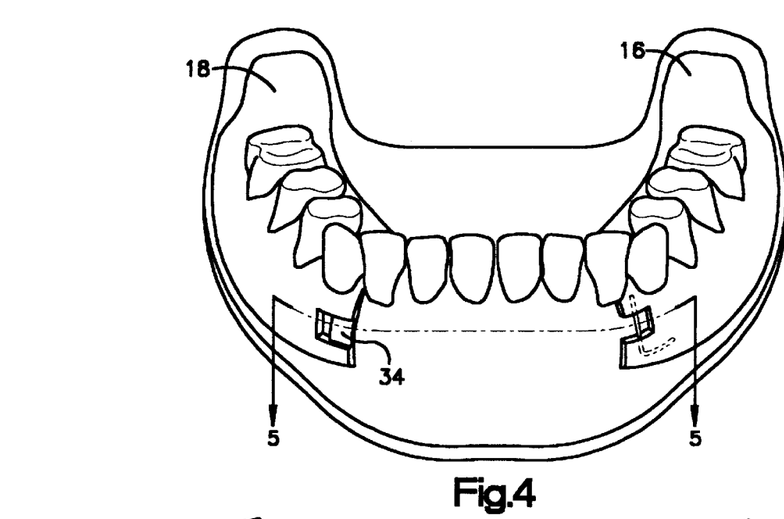
FIG. 4 is a perspective view of a partially formed dental appliance constructed in accordance with the present invention.

The second replacement tissue portion 18 includes the latch recess 34 with a configuration as shown in FIG. 4. At the end portion of the gate opposite the hinge is the protruding latch portion 32. The latch portion is configured and arranged to enable the gate to be swung closed around the abutment teeth and locked in place by inserting the latch portion into the latch recess. The latch portion 32 may be configured so as to be snap or pressure fit into the latch recess as shown in FIG. 2. The latch portion may also have other configurations such as a generally circular cross-section. The latch is fastened by pushing the latch portion so as to positively engage the retentative portion in the recess. The latch thus resists lateral forces and removal of the latch portion from the recess.

Figure 9:
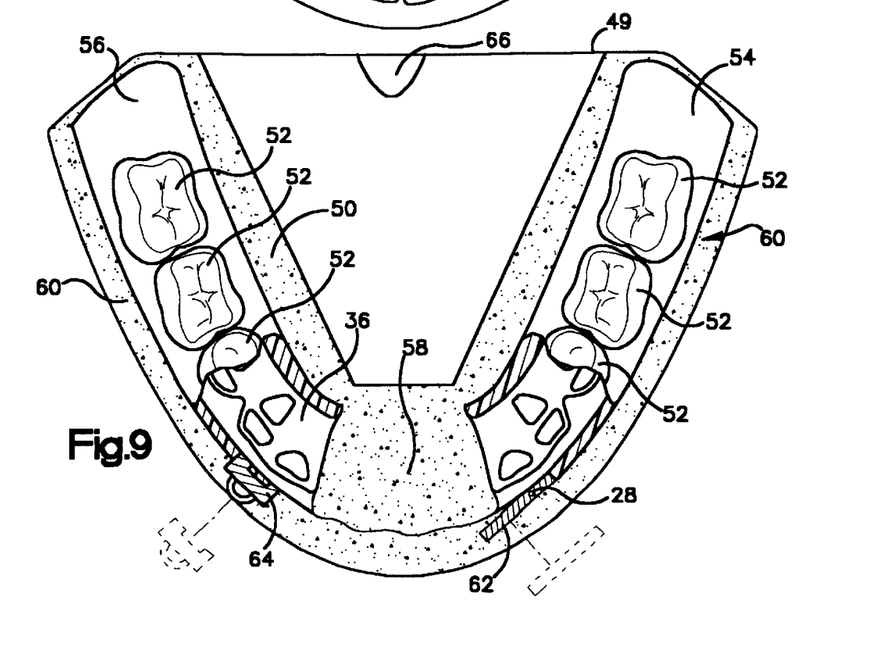
FIG. 9 is a top plan view of a wax-up of the framework invested in stone material of a portion of a flask for plastic injection.
Figure 10:
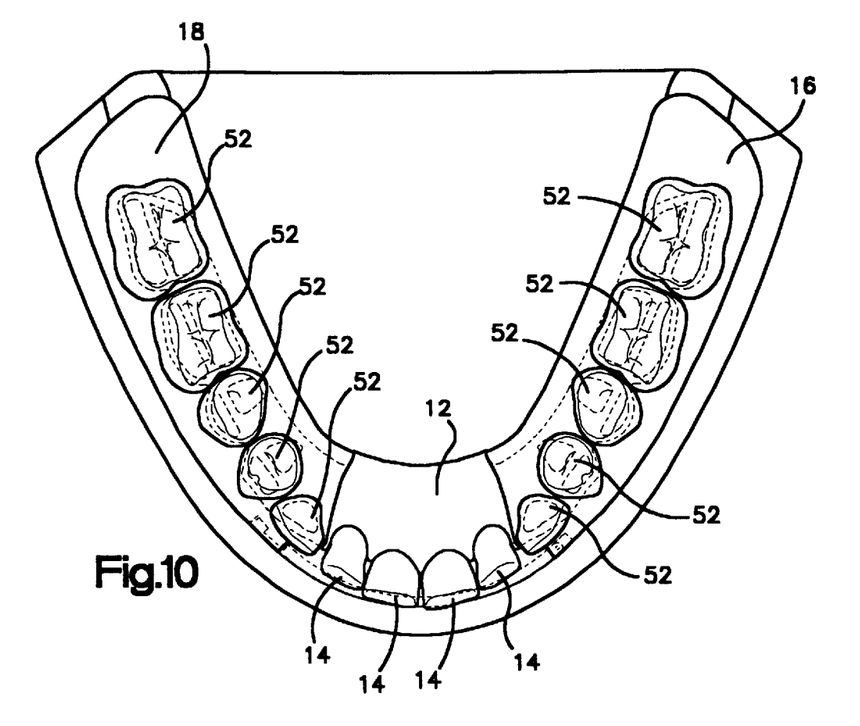
FIG. 10 is a top plan view of a dental appliance constructed in accordance with the present invention.

A method of making a new dental appliance utilizes a flask comprising two halves. The bottom half 44 of the flask has protruding alignment pins received in holes in the other half of the flask. A suitable dental "stone" may be used as the investment material 50, or a mixture of plaster and two thirds stone may be used. The investment material 50 is applied to the bottom half of the flask. The metal framework 36 is positioned on the investment material as shown in FIG. 9. The replacement teeth 52 are held in place in a wax-up of the first and second replacement tissue portions 54, 56 in the known manner. Alternatively, the replacement teeth may be completely supported in a wax-up of the first and second tissue replacement portions as one piece in the known manner without a metal framework. The wax-up metal framework or wax-up alone are invested to expose all replacement teeth, buccal and lingual. The investment material is preferably applied to cover the lingual section and the area where the abutment teeth will be located at 58, thereby exposing regions 60 that are intended to receive flexible, nonmetallic replacement tissue. Alternatively, only undercut portions of the tissue replacement portions, such as in the labial position, are covered with investment material, exposing the lingual section.

In the case of injecting curable nonmetallic material into the flask without the gate portion being present, a hinge recess-forming member 62 is positioned (e.g., around the hinge pin 28) in the investment mold material (FIG. 9). The hinge recess-forming member is preferably formed of a curable nonmetallic material (e.g., plastics, acrylics, resins) that will not adhere to the material of the tissue replacement portions. Alternatively, any hinge member that is to be formed as part of the first tissue replacement portion is formed as part of the wax-up and hinge components (forms) that are to be embedded in the nonmetallic material are held in the investment material.

A latch recess-forming member or form 64 is placed in the investment material in the intended position of the latch recess in the curable nonmetallic material. The latch recess-forming member is preferably formed of metal. Similarly, any components of the latch recess that are to be formed by curing may be formed in the wax-up of the second tissue replacement portion. Any components to form the latch may be positioned in the investment material so as to be embedded therein.

After the investment has set fully, the case of the invested framework may be sprued in the known manner at 66. The surface of the stone in the bottom half of the flask is covered with tinfoil substitute (such as Presto™ brand separating medium). The tinfoil substitute is allowed to dry thoroughly. The stone may be brushed over the teeth and convoluted areas. Then, the top half of the flask is placed in position to pour the remaining investment. The investment may be flowed into the flask by tapping the flask. After pouring, the two halves of the flask are secured together while the stone is setting.

Figures 5, 6A, 7:
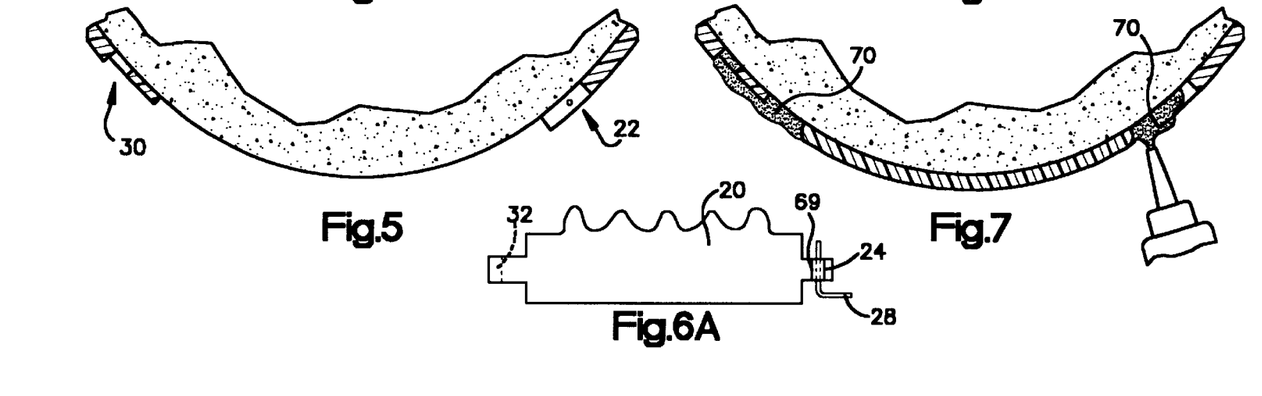
FIG. 5 is a cross-sectional view as seen along the plane designated by the arrows 5—5 in FIG. 4.
FIG. 6A is a view showing a tissue replacement gate.
FIG. 7 is a cross-sectional view as seen along the plane designated by the arrows 7—7 in FIG. 6.

After the stone has set, the flask is placed in a hot water bath for 10 minutes (6 minutes if boiling). The flask is removed from the water and the two halves are separated. The wax is washed out using wax remover. The two halves are cooled and all moisture evaporated. The replacement teeth may now be prepared for mechanical retention to the framework if this has not already been done. The entire stone surface is painted with tinfoil substitute and allowed to dry thoroughly. The flask is then closed securely. The resin is plasticized in the known manner and processed such as by packing, pouring or injecting into the flask. Then after the resin has set the two halves are separated. The nonmetallic material has hardened to form the first nonmetallic tissue replacement portion 16 extending from one end portion of the lingual section 12 and the second nonmetallic tissue replacement portion 18 extending from the other end portion of the lingual section. The replacement teeth 52 are held securely by the hardened nonmetallic material. The framework in each saddle section covered by a tissue replacement section or the all-plastic tissue replacement sections, is removed from the flask and the stone. The hinge recess-forming member 62 is removed, thereby forming the hinge recess 46 in the first tissue replacement portion. The latch recess-forming member 64 is removed, thereby forming the latch recess 34 in the second tissue replacement portion. The appliance now has a design as shown in FIGS. 4 and 5, illustrated in a dental mold.

Figure 6:
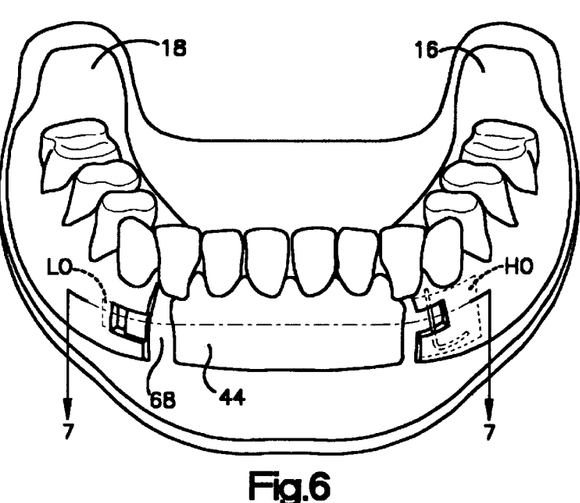
FIG. 6 is the partially formed dental appliance of FIG. 4 including a labial tissue replacement portion.

A wax form of the labial or buccal tissue replacement gate portion 44 is placed in an opening 68 of FIG. 6 between the hardened first tissue replacement portion and the hardened second tissue replacement portion. The wax form of the gate preferably has a final form as shown in FIG. 6A. This is supported in the flask by investment material. The wax is boiled off, exposing a region of the shape of the intended gate. The flask is injected with nonmetallic material such as plastic material filling the exposed regions. The nonmetallic material such as Valplast brand thermoplastic flows into the hinge recess around the hinge pin and into the latch recess forming the gate shown in FIG. 1. The injected nonmetallic material forms an accurate shape corresponding to the hinge and latch areas and yet, will not chemically bond to the first and second replacement tissue-forming portions. As a result, the latch portion of the gate may be removed from the latch recess and the gate will pivot in the first tissue replacement portion.

The portions of the appliance that carry the replacement teeth may be referred to as saddle sections in that they saddle the ridge in the mouth and are comprised of all tissue replacement material such as plastic or of the supportive framework embedded in the tissue replacement material. The hinge of the present invention may be a living hinge LH formed by continuous material between a saddle section and the gate as shown by the dotted lines in FIG. 1. The living hinge need not include the protruding hinge portion and the hinge recess, and would not include the hinge pin shown in FIG. 1. The gate 20 would move by bending along the line LH.

In the case of fabrication of the living hinge, a wax up of the gate and a wax up of a tissue replacement portion may be processed to remove the wax and form the cured material of the tissue replacement portion and the gate. Then, a wax up of the other tissue replacement portion is prepared and positioned in the investment material so as to produce the shape of the latch recess. This is then processed to remove the wax of the other tissue replacement portion and to form the tissue replacement portion from the cured material. This appliance would preferably be formed with a major connector (e.g., including the metal lingual section and framework sections) joining the saddle sections.

In the case of new appliance fabrication a nonmetallic (e.g., plastic) buccal or lingual gate 20 of the general shape shown in FIG. 6A may be positioned in the investment material, the gate including the hinge portion 24 having an optional cylindrical barrel 69 at an end thereof with a generally vertically extending opening that receives the hinge pin. The gate shown in FIG. 6A may be formed by any known manner such as using the lost wax process. Other hinges may also be suitably used as will be apparent to those skilled in the art in view of this disclosure, so as to take advantage of the nonmetallic (e.g., plastic) forming process of the present invention. The gate also includes the latch portion 32. The gate replaces the hinge recess-forming member 62 and the latch recess-forming member 64 that are shown in FIG. 9. The metal framework supporting the replacement teeth with wax-up first and second tissue replacement portions or the wax-up first and second tissue replacement portions supporting the replacement teeth without a metal framework, are also invested in position relative to the gate. The wax is removed as by boiling as described above and the nonmetallic (e.g., plastic) material is processed into the regions previously occupied by the wax to form the dental appliance shown in FIG. 1. The material of the gate such as Valplast™ brand thermoplastic does not adhere to the material of the first and second tissue replacement portions (such as the Valplast™ brand thermoplastic). Therefore, the hinge and latch portions of the gate by themselves form the corresponding hinge recess and latch recess in the first and second tissue replacement portions. In other words, the nonmetallic (e.g., plastic) hinge and latch portions of the gate function as the hinge recess and latch recess forming members 62, 64. The pin may be embedded in the nonmetallic (e.g., plastic) of the first tissue replacement portion and extends into the gate. After the appliance is removed from the stone, the latch portion of the gate may be removed from the latch recess and the gate may be swingably movable (such as around the pin) so that the abutment teeth are enclosed between the gate and the lingual section.

Another advantageous aspect of the invention is the ability to simply and efficiently restore dental appliances such as clasp-type partial dentures. Clasp-type partials typically include the first and second replacement tissue portions made of a plastic such as methacrylate and/or metal. As is well known, the partial includes metal or acrylic clasps that partially wrap around one or more abutment teeth to support the partial in the patient's mouth. In the inventive restoration process if a medical professional determines that use of the clasp-type dental appliance is no longer appropriate and that use of the inventive appliance is warranted, the clasps may be removed as by grinding. An opening HO (FIG. 6) for the hinge may be formed in the first (e.g., acrylic) tissue replacement portion and an opening LO for the latch may be formed in the second (e.g., acrylic) tissue replacement portion (these openings being shown in dotted lines). The latch opening is formed to approximate the final shape of the latch recess. Next, a nonmetallic (e.g., plastic) buccal or labial tissue replacement gate 20 (FIG. 6A) may be positioned in the opening between the first and second tissue replacement portions rather than the gate portion 44 shown in FIG. 6. A hinge component such as a pin may be disposed in the opening HO in the first tissue replacement portion. The latch portion of the gate is positioned in the latch opening LO. Next, secondary nonmetallic material 70 such as acrylic is applied as in FIG. 7 to the hinge opening. The nonmetallic material envelopes the hinge component (e.g., pin) and bonds to the first tissue replacement portion but does not bond to the gate portion which is formed of a different nonmetallic (e.g., plastic) material such as Valplast™ brand thermoplastic. The nonmetallic (e.g., plastic) material is also applied around the latch portion of the gate to the latch opening of the second tissue replacement portion. This produces the latch recess and provides a tight fit of the latch portion in the latch recess. The hardened secondary acrylic provides a strong bond to the acrylic of the first and second tissue replacement portions.

Another way to restore an existing dental appliance such as a clasp-type denture is to invest the appliance after the clasps have been removed, which may contain hinge and latch forms bonded to the hardened tissue replacement portions such as out of secondary acrylic. A wax up of the gate is then prepared and invested in the proper position relative to the forms. The wax is then removed and the curable material is applied to the exposed areas to form the cured gate with the mechanical hinge and gate connection. This construction takes advantage of the inability of the gate material to bond to the tissue replacement material. Other variations in restoring dental appliances such as partial clasp-type dentures in accordance with the invention would be apparent to one skilled in the art in view of this disclosure.

The first and second tissue replacement portions and the gate may be comprised of a suitable nonmetallic, curable material such as plastic material, more particularly a polymer material. The material is preferably an approved plastic material that possesses properties that prevent the material from bonding to itself. Some examples of suitable nonmetallic curable materials are materials comprising polyamides, copolyamides, acrylics such as methyl methacrylate, or acetyl resin. A suitable nonmetallic heat or self curing acrylic material comprises restoring methyl methacrylate for a denture base such as Frickie 808 brand pigmented denture base material (such as in powder form) dissolved in a suitable liquid monomer. A thermoplastic polymer is preferably used to facilitate forming by injection. However, portions of the hinge and latch recess may also be formed by applying cold cure methylmethacrylate to the first and second tissue replacement portions. The material of the end portion of the gate and, preferably of the entire gate, is preferably a suitable nonmetallic curable material that does not adhere to acrylics, since methacrylates are the typical dental material used to form the tissue replacement portions of partial dentures. It is advantageous in the forming process to fabricate the gate of a material that will not bond to the methacrylate partial denture material.

Some suitable nonmetallic curable materials for the gate are Valplast™ thermoplastics, Flexite Supreme™ brand copolyamide and Flexite Plus™ brand polyamide, such as are manufactured by Rapid Injections Systems Corp. The tissue replacement portions may be comprised of any of the above materials as well as any ADA approved restorative materials such as acrylics. In the case of new dental appliance fabrication, the tissue replacement portions and the labial gate may be formed of the same material such as one of the above listed plastics, except that acrylics maybe too brittle for the gate material. However, in new appliance fabrication the plastic tissue replacement portions (and in some cases the lingual section) may also be formed without the labial gate being present using the individual hinge recess-forming member 62 and the individual latch recess forming-member 64 as shown in FIG. 9 or the gate portion shown in FIG. 6A, in which case the labial gate may be formed of any nonmetallic curable (e.g., plastic) material that does not bond to the material of the tissue replacement portions. Suitable metals for the hinge pin and the framework are chrome cobalt alloys such as are disclosed in the 3,271,858 patent.

In the case of restoring dental appliances such as clasp-type partial dentures to utilize the design of the present invention, the gate may be formed of a different material than the tissue replacement portions. For example, in the case of restoring a dental appliance having acrylic tissue replacement portions (e.g., comprising methyl methacrylate), an acrylic-free gate portion is formed, for example, of Valplast™ brand thermoplastic, with the hinge portion and the latch portion. The gate portion of nonmetallic cured material is positioned in the opening 68 and the hinge member (e.g., hinge protrusion with the hinge pin) extends in the hinge opening while the latch member extends into the latch opening. Secondary nonmetallic curable material (e.g., acrylic) may then be applied to the latch opening and to the hinge opening. The secondary material thus forms a suitable enclosure adjacent the latch portion of the gate by bonding to the material (e.g., acrylic) of the second tissue replacement portion. The secondary material also bonds to the material (e.g., acrylic) of the first tissue replacement portion in the hinge opening and envelops the hinge component (e.g., hinge pin), while not bonding to the labial gate. This enables the gate to be swingably movable around the pin and to be latched closed by pushing the latch portion of the gate into the latch recess.

Although the invention has been described in its preferred form with a certain degree of particularity, it will be understood that the present disclosure of the preferred embodiments has been made only by way of example and that various changes may be resorted to without departing from the true spirit and scope of the invention as hereafter claimed.

What is claimed is:

1. A dental appliance comprising a lingual section adapted to engage at least one abutment tooth, a first tissue replacement portion extending from one end portion of said lingual section, a second tissue replacement portion extending from another end portion of said lingual section, a gate adapted to engage the at least one said abutment tooth at a buccal or labial position, wherein said gate extends between said first tissue replacement portion and said second tissue replacement portion when in a closed position so as to enclose the at least one said abutment tooth between said gate and said lingual section, and a hinge partially formed by an end portion of said gate, wherein said end portion of said gate is comprised of polymeric tissue replacement material.

2. The dental appliance of claim 1 comprising a latch disposed at another end portion of said gate which is adapted to retain said gate to said second tissue replacement portion when in the closed position.

3. The dental appliance of claim 2 wherein said latch is integrally formed with said gate.

4. The dental appliance of claim 1 wherein said gate is comprised of a poylmeric free from acrylic.

5. The dental appliance of claim 1 wherein said gate is comprised of a polymer material and is free from metal reinforcement.

6. The dental appliance of claim 1 wherein said gate is comprised of acetyl resin.

7. The dental appliance of claim 1 wherein said hinge is comprised of a mechanical interlocking of said end portion of said gate and a portion of said first tissue replacement portion.

8. The dental appliance of claim 7 wherein said hinge comprises a protruding portion from one of said gate and said first tissue replacement portion that extends into a recess of the other of said gate and said first tissue replacement portion and a hinge member about which said gate pivots relative to said first tissue replacement portion.

9. The dental appliance of claim 8 wherein portions of said hinge and said recess are comprised of secondary acrylic material bonded to acrylic material that comprises said first tissue replacement portion and said second tissue replacement portion.

10. The dental appliance of claim 1 wherein said hinge is a living hinge formed by polymeric material between said first tissue replacement portion and said gate.

11. A dental appliance comprising:

a lingual section adapted to engage at least one abutment tooth;

a first tissue replacement portion extending from one end portion of said lingual section;

a second tissue replacement portion extending from another end portion of said lingual section;

a gate adapted to engage the at least one said abutment tooth at a buccal or labial position, wherein said gate extends between said first tissue replacement portion and said second tissue replacement portion when in a closed position so as to enclose the at least one abutment tooth between said gate and said lingual section;

a hinge comprised of a mechanical interlocking between an end portion of said gate and a portion of said first tissue replacement portion that enables said gate to be swingably movable relative to said at least one abutment tooth, wherein said end portion of said gate is comprised of polymeric tissue replacement material; and a latch disposed at another end portion of said gate which is adapted to fasten said gate to said second tissue replacement portion.

12. The dental appliance of claim 11 wherein one of said one end portion of said gate and said first tissue replacement portion comprises a protrusion and the other of said one end portion of said gate and said first tissue replacement portion comprises a recess for receiving said protrusion, further comprising a pin that pivotably connects said end portion of said gate and said first tissue replacement portion.

13. The dental appliance of claim 12 wherein said hinge is a living hinge formed by polymeric material between said first tissue replacement portion and said gate.

14. The dental appliance of claim 12 comprising a first frame section disposed in said first tissue replacement portion and a second frame section disposed in said second tissue replacement portion, said first frame section and said second frame section being adapted to support replacement teeth.

15. The dental appliance of claim 14 wherein said lingual section, said first frame section and said second frame section are comprised of metal and integrally formed together.

16. The dental appliance of claim 12 wherein said first tissue replacement portion and said second tissue replacement portion are configured and arranged to support replacement teeth without a metal framework.

17. The dental appliance of claim 11 wherein said first tissue replacement portion and said second tissue replacement portion are comprised of acrylic tissue replacement portions from a clasp-type partial denture.

18. A method of making a dental appliance comprising the steps of:
  positioning a nonmetallic, polymeric buccal or labial gate portion in an opening between a first tissue replacement portion extending from one end portion of a lingual section and a second tissue replacement portion extending from another end portion of said lingual section, said first tissue replacement portion and said second tissue replacement portion being formed of polymeric tissue replacement material, said lingual section being adapted to engage at least one abutment tooth, said gate portion including a first hinge portion;
  positioning a hinge component in a recess of said first tissue replacement portion, said hinge component being adapted to be carried by said gate;
  applying secondary polymeric tissue replacement material which is incapable of bonding to said gate polymeric material but bonds to said polymeric tissue replacement material to said recess so as to interconnect said hinge component and said first tissue replacement portion; and
  hardening said polymeric tissue replacement material such that said gate portion is swingably movable about said hinge component relative to said at least one abutment tooth.

19. The method of claim 18 further comprising positioning a latch form portion of said polymeric gate configured and arranged in the form of a latch member in an opening formed in said second polymeric tissue replacement portion, applying secondary polymeric tissue replacement material which is incapable of bonding to said gate polymeric material but bonds to said polymeric tissue replacement material to said opening formed in said second tissue replacement portion and hardening said secondary polymeric material to form a latch recess around said latch form portion bonded to said second tissue replacement portion such that said latch member can be fastened in said latch recess.

20. The method of claim 18 wherein said first tissue replacement portion, said second tissue replacement portion and said lingual section form part of a clasp-type dental appliance, comprising removing clasps from said clasp-type dental appliance and forming said hinge opening in said first tissue replacement portion of said clasp-type appliance.

21. The method of claim 18 wherein said polymeric tissue replacement material is formed of acrylic and said secondary polymeric tissue replacement material is comprised of acrylic.

22. A method of making a dental appliance comprising the steps of:
  positioning a replacement tooth-supporting member in investment mold material contained by a vessel, said member including a first tissue replacement portion comprised of wax which extends from an end portion of a lingual section adapted to engage at least one abutment tooth and a second tissue replacement portion which extends from another end portion of said lingual section;
  positioning a buccal or labial gate in said investment mold material, said gate including a hinge form including a hinge pin and configured and arranged to form a hinge component in said wax of said first tissue replacement portion and a latch form configured and arranged in the shape of a latch component in said wax of said second tissue replacement portion, said gate being formed of gate polymeric material;
  removing said wax to expose regions of said first and second tissue replacement portions and regions configured and arranged in the shape of a hinge component and a latch void which are intended to receive polymeric tissue replacement material;
  applying said polymeric tissue replacement material to said exposed regions, said polymeric tissue replacement material being incapable of bonding to said polymeric gate material;
  hardening said polymeric tissue replacement material to form a first polymeric tissue replacement portion extending from one end portion of said lingual section, a second polymeric tissue replacement portion extending from another end portion of said lingual section, said hinge component in said first tissue replacement portion and a latch recess in said second tissue replacement portion about said latch component;
  whereby said gate has a hinge component that interacts with said hinge component of said first tissue replacement portion and is adapted to pivot about said hinge pin embedded in said first tissue replacement portion and a latch portion that is adapted to fit into said latch recess, wherein said gate encloses the at least one said abutment tooth between said gate and said lingual section when said gate is in a closed position.

23. A gate for a dental appliance, said gate having a body which has a curvature and is shaped so as to be adapted to approximate a buccal or labial tissue replacement portion, said gate being comprised of cured polymeric tissue replacement material and is free from metal reinforcement, said gate comprising a hinge component formed integrally therewith and a latch component formed integrally therewith.

24. The gate of claim 23 further comprising a hinge pin carried by said hinge component.

25. A method of making a dental appliance comprising the steps of:
  positioning a replacement tooth-supporting member in investment mold material contained by a vessel, said member including tissue replacement portions comprised of wax;
  positioning a hinge form in said investment mold material and in said wax of one of said tissue replacement portions, said hinge form being configured and arranged to include a hinge pin and hinge recess which are formed of material which does not bond to polymeric tissue replacement material;
  positioning a latch form in said investment mold material and in said wax of another of said tissue replacement portions, said latch form being configured and arranged in the shape of a latch component formed of a material which does not bond to polymeric tissue replacement material;
  applying said investment mold material to cover a location intended to receive a gate located at a buccal or labial position;
  removing said wax tissue replacement portions to expose regions that are intended to receive polymeric tissue replacement material;
  applying said polymeric tissue replacement material to said exposed regions;

hardening said material to form a first tissue replacement portion extending from one end portion of said lingual section and a second tissue replacement portion extending from another end portion of said lingual section;

removing said hinge form to form a hinge recess in said first tissue replacement portion and a hinge pin embedded within said first tissue replacement portion;

removing said latch form to form a latch recess in said second tissue replacement portion;

removing said investment mold material;

applying wax to said location, said hinge recess and said latch recess to form a shape corresponding to a gate extending between said first tissue replacement portion and said second tissue replacement portion and positioning said wax in an investment mold material contained by a vessel;

removing said wax to form exposed gate voids at said location, said hinge recess and said latch recess in said investment mold material;

applying polymeric gate material to said exposed gate voids, said polymeric gate material being incapable of bonding to said polymeric tissue replacement material; and hardening said polymeric gate material to form a gate having a hinge portion extending in said hinge recess around said hinge pin and a latch portion in said latch recess so as to enclose the at least one said abutment tooth between said gate and said lingual section when said gate is in a closed position.

26. A method of making a dental appliance comprising the steps of:

forming a hinge opening in a first tissue replacement portion extending from one end portion of a lingual section which is adapted to engage at least one abutment tooth, a second tissue replacement portion extending from another end portion of said lingual section, said first tissue replacement portion and said second tissue replacement portion being formed of polymeric tissue replacement material;

positioning a hinge form including a hinge component in said opening of said first tissue replacement portion, said hinge form being incapable of bonding to said polymeric tissue replacement material;

applying secondary polymeric tissue replacement material, which is incapable of bonding to gate polymeric material but bonds to said polymeric tissue replacement material, in said opening so as to interconnect said hinge component and said first tissue replacement portion while not bonding to said hinge form, removing said hinge form to form a hinge recess;

positioning a wax buccal or labial gate portion in investment mold material contained by a vessel in an opening between said first polymeric tissue replacement portion and said second polymeric tissue replacement portion, said gate portion including a first hinge portion received by said hinge recess and disposed around said hinge component;

removing said wax gate portion to form exposed regions between said first tissue replacement portion and said second tissue replacement portion and a hinge void around said hinge component;

applying said gate polymeric material to said exposed regions and said hinge void; and hardening said gate polymeric tissue replacement material to form a gate having a first hinge portion in said hinge void around said hinge component such that said first hinge portion pivots about said hinge component relative to said first tissue replacement portion and said abutment tooth is enclosed between said gate and said lingual section when said gate is in a closed position.

27. The method of claim 26 further comprising forming a latch opening in said second polymeric tissue replacement portion;

positioning a latch form in said latch opening, said latch form being incapable of bonding to said polymeric tissue replacement material;

applying secondary polymeric tissue replacement material, which is incapable of bonding to said gate polymeric material but bonds to said polymeric tissue replacement material, in said latch opening without bonding to said latch form;

removing said latch form to form a latch recess;

hardening said secondary polymeric tissue replacement material;

positioning said wax buccal or labial gate portion in investment mold material contained by the vessel in said opening between said first polymeric tissue replacement portion and said second polymeric tissue replacement portion, said gate portion including a latch portion configured and arranged to be received in said latch recess;

removing said wax gate portion to form exposed regions between said first tissue replacement portion and said second tissue replacement portion and a latch void at said latch recess;

applying said gate polymeric material to said exposed regions and said latch void; and hardening said gate polymeric tissue replacement material to form a latch portion as part of said gate which is received by said latch void so as to retain said gate in the closed position.

28. A dental appliance comprising a lingual section adapted to engage at least one abutment tooth, at least one polymeric tissue replacement portion extending from an end portion of said lingual section and carrying replacement teeth, a gate adapted to engage the at least one said abutment tooth at a buccal or labial position, and a hinge about which said gate is pivotally connected to the at least one said tissue replacement portion, wherein said gate extends from the at least one said tissue replacement portion when in a closed position so as to enclose the at least one said abutment tooth between said gate and said lingual section, wherein said gate is comprised of polymeric material which is free from metal reinforcement and incapable of bonding to said polymeric tissue replacement portion and includes an integral polymeric portion which is configured and arranged so as to be operatively associated with a complementary shaped portion of the at least one said tissue replacement portion in close tolerance.

* * * * *